United States Patent
Baier-Goschütz et al.

(10) Patent No.: US 10,625,241 B2
(45) Date of Patent: Apr. 21, 2020

(54) HEMOCOMPATIBLE ADSORBER FOR THE DIALYSIS OF PROTEIN-BOUND UREMIC TOXINS

(71) Applicant: B. BRAUN AVITUM AG, Melsungen (DE)

(72) Inventors: Angela Baier-Goschütz, Bad Gottleuba-Berggiesshübel (DE); Alexander Friebe, Recklinghausen (DE); Roland Napierala, Werther (DE); Juliane Gäbler, Pulsnitz (DE)

(73) Assignee: B. Braun Avitum AG (DE)

( * ) Notice: Subject to any disclaimer, the term of this patent is extended or adjusted under 35 U.S.C. 154(b) by 0 days.

(21) Appl. No.: 15/969,306

(22) Filed: May 2, 2018

(65) Prior Publication Data

US 2018/0369783 A1    Dec. 27, 2018

(30) Foreign Application Priority Data

Jun. 22, 2017   (DE) .................. 10 2017 113 853

(51) Int. Cl.
*B01J 20/24* (2006.01)
*B01J 20/28* (2006.01)
(Continued)

(52) U.S. Cl.
CPC ............ *B01J 20/24* (2013.01); *A61M 1/3486* (2014.02); *A61M 1/3679* (2013.01);
(Continued)

(58) Field of Classification Search
CPC .............. A61M 1/3413; A61M 1/3486; A61M 1/3679; B01J 20/24; B01J 20/265;
(Continued)

(56) References Cited

U.S. PATENT DOCUMENTS

| 4,140,652 A | 2/1979 | Korshak et al. |
| 4,634,604 A | 1/1987 | Tlustakova et al. |

(Continued)

FOREIGN PATENT DOCUMENTS

| DE | 109363 | 11/1974 |
| EP | 0129905 A2 | 1/1985 |

(Continued)

OTHER PUBLICATIONS

Biros et al., "Structure and Binding Properties of Water-Soluble Cavitands an Capsules", Chem. Soc. Rev., 2007, 36, pp. 93-104.
(Continued)

*Primary Examiner* — Dirk R Bass
(74) *Attorney, Agent, or Firm* — RatnerPrestia

(57) ABSTRACT

A hemocompatible adsorber for separating protein-bound uremic toxins contained in the blood of a patient and having a molecular mass of <500 g/mol regarding their carrier proteins, to adsorb the uremic toxins during hemodialysis. The hemocompatible adsorber including a polymer based on a cyclic oligosaccharide or a derivative thereof which is disposed on a solid carrier component. A device for hemodiafiltration including an extracorporeal circuit for receiving blood to be purified and a hemodialyzer connected to the blood circulation of a patient, wherein a hemocompatible adsorber is provided for separating protein-bound uremic toxins contained in the blood of a patient and having a molecular mass of <500 g/mol regarding their carrier proteins. The hemocompatible adsorber, which is disposed on a solid carrier component in at least one layer on the blood side within the hemodialyzer, includes a polymer based on a cyclic oligosaccharide or a derivative thereof.

16 Claims, 1 Drawing Sheet

(51) Int. Cl.
| | |
|---|---|
| A61M 1/34 | (2006.01) |
| B01J 20/30 | (2006.01) |
| B01J 20/32 | (2006.01) |
| B01J 20/26 | (2006.01) |
| A61M 1/36 | (2006.01) |

(52) U.S. Cl.
CPC .......... *B01J 20/265* (2013.01); *B01J 20/267* (2013.01); *B01J 20/28038* (2013.01); *B01J 20/3085* (2013.01); *B01J 20/321* (2013.01); *B01J 20/3208* (2013.01); *B01J 20/3212* (2013.01); *B01J 20/3221* (2013.01); *B01J 20/3274* (2013.01); *B01J 20/3282* (2013.01); *B01J 20/3289* (2013.01); *A61M 1/3413* (2013.01); *B01J 2220/4825* (2013.01)

(58) Field of Classification Search
CPC ............... B01J 20/267; B01J 20/28038; B01J 20/3085; B01J 20/3208; B01J 20/321; B01J 20/3212; B01J 20/3221; B01J 20/3274; B01J 20/3282; B01J 20/3289; B01J 2220/4825
See application file for complete search history.

(56) References Cited

U.S. PATENT DOCUMENTS

| | | | |
|---|---|---|---|
| 4,889,634 A | 12/1989 | El-Rashidy | |
| 2004/0226874 A1* | 11/2004 | Nanko | A61M 1/3679 210/266 |
| 2008/0312575 A1* | 12/2008 | Graziani | B01D 69/105 604/5.02 |
| 2010/0040674 A1* | 2/2010 | Smith | A61K 9/7007 424/443 |
| 2012/0027837 A1* | 2/2012 | DeMuth | A61K 9/0021 424/443 |
| 2017/0189599 A1* | 7/2017 | Menzel Bueno | A61M 1/1603 |

FOREIGN PATENT DOCUMENTS

| | | | |
|---|---|---|---|
| EP | 2918337 A1 | 9/2015 | |
| GB | 1466702 | 3/1977 | |
| WO | 2007013122 A1 | 2/2007 | |
| WO | 2009157877 A1 | 12/2009 | |
| WO | 2010045474 A2 | 4/2010 | |
| WO | 2015091842 A2 | 6/2015 | |
| WO | 2015136107 A1 | 9/2015 | |

OTHER PUBLICATIONS

Brewster et a., "Cyclodextrins as Pharmaceutical Solubilizers", Advanced Drug Delivery Reviews 59 (2007) pp. 645-666.
Chen et al., "Development of a Layer-by-Layer Assembled Film on Hydrogel for Ocular Drug Delivery", International Journal of Popular Science, vol. 2015, 2015, 9 pages.
Cravatto, "Enabling Technologies and Green Processes in Cyclodextrin Chemistry", Beilstein Journal of Organic Chemistry, 2016, 12, pp. 278-294.
Cytosorbents, Product Information, https://cytosorbents.com, retrieved Apr. 19, 2018, 2 pages.
German Search Report for German Application No. 10 2017 113 853.6, dated Dec. 22, 2017—15 pages.
Glorieux et al., "Uraemic Toxins and New Methods to Control their Accumulation: Game Changers for the Concept of Dialysis Adequacy", Clinical Kidney Journal, 2015, vol. 8, No. 4, pp. 353-362.
Pavlenko et al., "New Low-flux Mixed Matrix Membranes that offer Superior Removal of Protein-bound Toxins from Human Plasma", Scientific Reports, published Oct. 5, 2016—pp. 1-10.
Pédehontaa-Hiaa et al., "Layer-by-Layer Assemblies on a Cationic β-Cyclodextrin Polymer: Chiral Stationary Phases for Open-Tubular Electrochromatography", Chromatographia 2015, 78: pp. 533-541.

Smith et al., "Layer-by-Layer Platform Technology for Small-Molecule Delivery", Angew. Chem. Int. Ed., 2009, 48, pp. 8974-8977.
Tette et al., Removal of Cytokines and Activated Complement Components in an Experimental Model of Continuous Plasma Filtration Couples with Sorbent Adsorption, Nephrol Dial Transplant (1998) 13, pp. 1458-1464.
Vanholder et al., "Assessment of Urea and Other Uremic Markers for Quantification of Dialysis Efficacy", Clinical Chemistry, vol. 38, No. 8, 1992, pp. 1429-1436.
Vanholder et al., "Review on Uremic Toxins: Classification, Concentration, and Interindividual Variability," Kidney International, vol. 63 (2003), pp. 1934-1943.
Zheng et al., "Supramolecular Nanostructures Based on Cyclodextrin and Poly(ethylene oxide): Syntheses, Structural Characterizations and Applications for Drug Delivery", Polymers, 2016, 8, 198—18 pages.
Alsbaiee et al., "Rapid Removal of Organic Micropollutants from Water by a Porous β-cyclodextrin Polymer", Nature 2016; vol. 529—17 pages.
CytoSorb™, http://02c390e.netsolhost.com/pdf/CytoSorb_Product_Brochure_March_2012.pdf—4 pages.
CytoSorb™ 300mL Device—Instructions for Use, May 18, 2012, www.cytosorb.com—2 pages.
Hazenbrink, D., "Combined publication of ERA-EDTA 2014 abstracts, Haemodialysis Techniques and Adequacy 1" Nephrology Dialysis Transplantation 29 (supplement 3): vol. 29, May 2014—pp. 209-222.
Hoenich et al., "Clinical Comparison of High-flux Cellulose Acetate and Synthetic Membranes", Nephrol Dial Transplant 1994; 9: pp. 60-66.
Jicsinszky et al., "Nucleophilic Substitutions of 6 0-Monotosyl-β-cyclodextrin in a Planetary Ball Mill", Sustainable Chem Eng 2016; 4: pp. 919-929.
Jindal et al., "A Study of the Basic Principles Determining the Performance of Several High-flux Dialyzers", American Journal of Kidney Disease, vol. XIV, No. 6 Dec. 1989—pp. 507-511.
Lv et al., "Preparation and Characterization of Poly-carboxymethyl-β-cyclodextrin Superplasticizer", Cement and Concrete Research 2012; 42: pp. 1356-1361.
Menuel et al., "Selective Secondary Face Modification of Cyclodextrins by Mechanosynthesis.", J Org Chem 2015; 80:6259-6266.
Niwa et al., "Organic Acids and the Uremic Syndrome: Protein Metabolite Hypothesis in the Progression of Chronic Renal Failure", Semin Nephrol 1996; 16: pp. 167-182.
Shaw et al., Selective Removal of Bitter Compounds from Grapefruit Juice and from Aqueous Solution with Cyclodextrin Polymers and with Amberlite XAD-4. J. Agric. Food Chem., 1986; 34: pp. 837-840.
Tijink et al, "A Novel Approach for Blood Purification: Mixed-matrix Membranes Combining Diffusion and Adsorption in One Step", Acta Biomaterialia 2012; 8: pp. 2279-2287.
Vanholder et al., "Uremic Toxicity: The Middle Molecule Hypothesis revisited", Seminars in Nephrology, vol. 14, No. 3 May 1994, pp. 205-218.
Extended European Search Report for European Application No. 18176248.5, with English translation, dated Nov. 13, 2018—20 pages.
Junthip et al., "Layer-by-Layer Coating of Textile with Two Oppositely Charged Cyclodextrin Polyelectrolytes for Extended Drug Delivery, Intrisic Antibacterial Activity of Multilayer Assemblies", Journal of Biomedical Materials Research, Part A, vol. 104, No. 6, Feb. 2, 2016—pp. 1408-1424.
Martel et al., "Grafting of Cyclodextrins onto Polypropylene Non-woven Fabrics for the Manufacture of Reactive Filters. III. Study of the Sorption Properties", Journal of Applied Polymer Science, vol. 85, No. 8, Aug. 22, 2002—pp. 1771-1778.
Zhao et al., "Synthesis and Characterization of Polymer-immobilized Beta-cyclodextrin with an Inclusion Recognition Functionality", Reactive Polymers, Elsevier Science Publishers, Amsterdam, NL, vol. 24, No. 1, Nov. 1, 1994—pp. 9-16.

\* cited by examiner

HEMOCOMPATIBLE ADSORBER FOR THE DIALYSIS OF PROTEIN-BOUND UREMIC TOXINS

CROSS REFERENCE TO RELATED APPLICATIONS

This application claims priority to German application DE 10 2017 113 853.6 filed Jun. 22, 2017, the contents of such application being incorporated by reference herein.

FIELD OF THE INVENTION

The present invention relates to a hemocompatible adsorber and a device for hemodiafiltration according to the independent claims.

BACKGROUND OF THE INVENTION

From the physiology of the kidney, it is generally known that it is the task of a healthy kidney to excrete end products of the metabolism as so-called "urinary substances" and toxins, so-called "uremic toxins" from the body via the urine. The kidney removes a broad spectrum of substances of different molecular masses. An overview of uremic toxins has been published by Vanholder et al. in 2003. [see Vanholder et al., Kidney International, 63 (2003) 1934-1943]. The uremic toxins are essentially divided into three classes on the basis of their molecular masses:

A) Low molecular mass toxins having a molecular mass of <500 g/mol;

B) toxins having an average molecular mass, also known as "mean molecules", which have a molecular mass between 500 and 12,000 g/mol. For example, the medium molecules include β2-microglobulin (11800 g/mol).

C) The third class of uremic toxins are molecules with a molecular mass of >12,000 g/mol.

In addition, a distinction is made regarding the water solubility of the uremic toxins. Examples of highly water-soluble uremic toxins with a low molecular mass are urea, creatinine, oxalates, guanidine and uric acid.

Examples of poorly water-soluble uremic toxins are p-cresol, indoxyl sulfate, phenol, hippuric acid and homocysteine. These uremic toxins are mainly present in the serum in the form of being bound to proteins.

In healthy individuals, uremic toxins are excreted via the kidneys with urine. In chronic kidney failure, however, these toxins remain in the patient's blood and must be removed by hemodialysis or peritoneal dialysis.

While the removal of water-soluble toxins such as urea or creatinine with hemodialysis is very well possible, the removal of poorly water-soluble hydrophobic uremic toxins by hemodialysis is extremely difficult due to protein binding, since protein-bound uremic toxins are only accessible via the chemical equilibrium of the toxin-protein complex with free toxin in the blood plasma of hemodialysis, the equilibrium being strongly on the side of the complex. This means that the major part of uremic toxins is bound to proteins, while only a small portion is dissolved in the blood plasma and only these free uremic toxins can be dialyzed.

Further studies on the physiological chemistry of protein-bound uremic toxins have shown that human serum albumin acts as a binding partner of hydrophobic uremic toxins and thus toxin-albumin complexes form in the blood of the patient.

Albumin is retained by common dialysis membranes due to its molecular mass of approx. 65,000 g/mol. Albumin is therefore not removed by hemodialysis. This means that only the free, dissolved and very small proportion of uremic toxins can be removed from the patient's blood. After the removal of this small free portion, the balance between albumin-bound and free uremic toxins is restored.

Theoretically, this rebalancing could remove a significant proportion of the free uremic toxins by continuous dialysis. However, the association constants of the toxin-albumin complex as well as an insufficiently practicable dialysis time are in conflict with this.

For a long time now, there has therefore been a need for dialysis methods that are capable of effectively removing protein-bound uremic toxins from the blood of patients with chronic kidney failure or chronic intense renal insufficiency.

DESCRIPTION OF THE RELATED ART

There are already a number of prior art approaches to this, but for various reasons none of them have been accepted in everyday clinical practice.

The following references to Literature, which are incorporated fully by reference herein, are referred to throughout the description.

Literature

[1] Vanholder R, De Smet R, Hsu C, Vogcleere P, Ringoir S. Uraemic toxicity: the middle molecule hypothesis revisited. Semin Nephrol 1994; 14: 205-218

[2] Bergström J. Uraemic toxicity. In: Kopple J D, Massry S G (eds). Nutritional Management and Renal Disease. Williams et. Wilkins, Baltimore, 1997; 97-190

[3] Hoenich N A, Woffindin C, Matthews J N S, Goldfinch M E. Turnbull J. Clinical comparison of high-flux cellulose acetate and synthetic membranes. Nephrol Dial Transplant 1994; 9: 60-66

[4] Jindal K K, McDougall J, Woods B, Nowakowski L, Goldstein M B. A study of the basic principles determining the performance of several high flux dialyzers. Am 3 Kidney Dis 1989; 14: 507-511

[5] Vanholder R, De Smet R, Ringoir S. Assessment of urea and other uremic markers for quantification of dialysis efficacy. Clin Chem 1992; 38: 1429-1436

[6] Niwa T. Organic acids and the uremic syndrome: protein metabolite hypothesis in the progression of chronic renal failure. Semin Nephrol 1996; 16:167-182

[7] DD 109 363, Von einem Polymer umschlossene Aktivkohle, Sparks et al.

[8] WO 2015 136107A1, Adsorbergranulat zur Entfernung urämischer Toxine, Tschulena et al.

[9] Pavlenko D, van Gereffen, van Steenbergen M J, Glorieux G, Vanholder R, Gerritesen K G F, Stamatialis D F. New low-flux mixed matrix membranes that offer superior removal of protein-bound toxins from human plasma. Nature, Scientific Reports 2016; DOI: 10.1038/srep34429: 1-9

[10] Tijink M S L, Wester M, Sun J, Saris A, Bolhuis-Versteeg L A M, Saiful S, Joles J A, Borneman Z, Wessling M, Stamatialis D F. A novel approach for blood purification: Mixed-matrix membranes combining diffusion and adsorption in one step. Acta Biomaterialia 2012; 8: 2279-2287

[11] a: Glorieux et al., Uremic toxins and new methods to control their accumulation: game changers for the concept of dialysis adequacy, Clinical Kidney Journal 2015; 8: 353-362 b: Krieter et al., Pilot trial on ionic strength hemodiafiltration, a novel dialysis technique for increased protein bound toxin removal, Poster EDTA 2014

[12] Dissertation Falko Böhring, Entwicklung klinischer Methoden zur vermehrten Abtrennung proteingebundener Urämie-Toxine im Rahmen einer extrakorporalen Therapie, Berlin 2013

[13] EP 0 129 905 A2, Poröse synthetische Sorbentien mit biokompatibler Oberfläche and ihre Herstellung. Tlustakova et al.

[14] Produktinformation Cytosorb, Fa. CytoSorbens Inc. NJ 08852 USA, 2012

[15] WO 2015/091842 A2, Method for removing protein-bound uremic toxins by adsorption to auxiliary substances that can be subjected to dialysis, Fislage et al.

[16] Smith R C, Riollano M, Leung A, Hammond P T. Layer-by-Layer Platform Technology for Small-Molecule Delivery. Angew. Chem. Int. Ed. 2009; 48: 8974-8977

[17] Dissertation Nina Zeh, In-vitro Versuche zur Entfernbarkeit von Furansäure, Indoxylsulfat und Pentosidin im Plasma von chronischen Hämodialysepatienten mittels Albumindialyse, Berlin 2009

[18] Dissertation Carotin Thiele, Synthese von Cyclodextrin-und Stärkederivaten zum verbesserten Wirkstofftransport, Saarbrücken 2010

[19] Tetta C, Cavaillon J M, Schulze M, Ronco C, Ghezzi P M, Camussi G, Serra A M, Lonnemann F C et G. Removal of cytokines and activated complement components in an experimental model of continuous plasma filtration coupled with sorbent adsorption. Nephrol Dial Transplant 1998; 13: 1458-1464

[20] Pedehontaa-Hiaa G, Guerrouache M, Carbonnier B, Le Derf F, Morin C J. Layer-by-Layer Assemblies Based on a Cationic β-Cyclodextrin Polymer: Chiral Stationary Phases for Open-Tubular Electrochromatography. Chromatographia 2015; 78: 533-541

[21] Chen P, Wang X, Dong Y, Hu X. Development of a Layer-by-Layer Assembled Film on Hydrogel for Ocular Drug Delivery. Int J of Polymer Sc 2015; Article ID 535092 (9 pages)

[22] Lv S, Gao R, Cao Q, Li D, Duan J. Preparation and characterization of poly-carboxymethyl-β-cyclodextrin superplasticizer. Cement and Concrete Research 2012; 42:1356-1361

[23] Alsbaiee A, Smith B J, Xiao L, Ling Y, Helbling D E, Dichtel W R. Rapid removal of organic micropollutants from water by a porous β-cyclodextrin polymer. Nature 2016; 529: 790-794/206

[24] Jicsinszky L, Caporaso M, Tuza K, Martina K, Gaudino E C, Cravotto G. Nucleophilic Substitutions of 6 0-Monotosyl-β-cyclodextrin in a Planetary Ball Mill. Sustainable Chem Eng 2016; 4:919-929

[25] Menuel S, Doumert B, Saitzek S, Ponchel A. Delevoye L, Monlier E, Hapiot F. Selective Secondary Face Modification of Cyclodextrins by Mechanosynthesis. J Org Chem 2015; 80:6259-6266

[26] Shaw P E, Buslig B S. Selective Removal of Bitter Compounds from Grapefruit Juice and from Aqueous Solution with Cyclodextrin Polymers and with Amberlite XAD-4. J Agric Food Chem 1986; 34: 837-840

[27] Zheng Y, Wyman I W. Supramolecular Nanostructures Based on Cyclodextrin an Poly(ethylene oxide): Synthesis, Structural Characterizations and Applications for Drug Delivery. Polymers 2016; 8: 198 (18 pages)

An overview of uremic toxins has been published by Vanholder et al. in 2003. [see Vanholder et al., Kidney International, 63 (2003) 1934-1943].

GB 1 466 702 discloses polymer-coated activated carbon for the adsorption of uremic toxins in the digestive tract.

The use of polymer-coated activated carbon for the adsorption of uremic toxins from blood is known from U.S. Pat. No. 4,140,652.

WO 2009/157877 discloses a process for the removal of toxins from a dialysis fluid by adsorption to $ZrO_2$ particles.

Furthermore, WO 2010/045474 discloses a competitive method for the separation of protein-bound uremic toxins by adding a substance that displaces the toxins from their binding sites on the protein and thus makes them available for dialysis.

U.S. Pat. No. 4,889,634 further discloses a solution for peritoneal dialysis containing hydroxypropyl-β-cyclodextrin.

In summary, it can be concluded that the adjustment of the equilibrium between protein-bound, especially albumin-bound uremic toxins and freely available uremic toxins under dialysis conditions is the speed-determining step. As mentioned above, although it is to be expected that the balance between free and protein-bound toxins will be restored after the removal of the dissolved toxins from the blood and that a considerable portion of the toxins can be removed if dialysis time is sufficiently long, this time is not available for hemodialysis treatments.

During dialysis, albumin is retained by the usual dialysis membranes due to its molecular mass and thus also the toxins bound to it.

However, if according to WO2015091842 A2 [15] the protein-bound uremic toxins are transferred to a low-molecular mass binding partner (instead of the high-molecular mass protein partner) so that the resulting complex of binding partner and uremic toxin has a molecular mass which is in the dialyzable area, the toxin present in free solution as well as the toxin previously present in albumin bond can be removed when passing through the dialyzer. Such low-molecular weight binding partners are added to dialyses as dialyzable adjuvants in the context of the disclosure of document [15].

In accordance with document [15], it is proposed in particular to dose a dialyzable excipient for instance into the blood supply hose of a dialyzer, so that the desired balance between binding partner and toxin is established on the way to the dialyzer. In this process, the toxin is removed from its binding sites on albumin or other proteins. The binding partner with the bound toxin can then be removed efficiently by a conventional dialysis method. As such competitive excipients, WO2015091842 A2 proposes to use, among other things, cyclodextrins with molecular masses ranging from 500 to 5,000 g/mol, preferably 1,000 to 2,000 g/mol.

The substance class of cyclodextrins is known to bind hydrophobic compounds.

Cyclodextrins are a class of compounds belonging to the cyclic oligosaccharides. They represent ring-shaped degradation products of starch. They consist of α-1,4-glycosidically linked glucose molecules. This results in a toroidal structure with a central cavity. Depending on the number of glucose molecules linked, they receive a Greek letter as a prefix:

The properties of cyclodextrins such as water solubility can be influenced by substitution of hydroxyl groups. For example, the water solubility of β-cyclodextrin is increased by methyl substitution by a factor of 150. Furthermore, the adsorption properties of cyclodextrins can be altered by selective substitution. For example, β-cyclodextrin may not be administered intravenously as it forms insoluble complexes with cholesterol. The substituted cyclodextrins hydroxypropyl-β cyclodextrin (HPBCD) and sulfobutyl ether-β-cyclodextrin (SBECD) do not form insoluble cholesterol complexes and are therefore preferred cyclodextrins for use in accordance with document [15].

In addition to the above-mentioned cyclodextrin compounds, there are other derivatives of the various cyclodextrin base species that are candidates for the application according to aspects of the invention. They are known to the person skilled in the art from review articles such as that from Brewster et al. (Advanced Drug Delivery Reviews 59 (2007) 645-666) and are generally distinguished by the introduction of hydrophilic groups of substitutable groups of the cyclodextrin molecule.

In principle, in addition to cyclodextrins, other macrocyclical systems with comparable structural properties can also be considered. The review by Biros et al. (Chem. Soc. Rev., 2007, 36, 93-104) gives an overview to this. In addition to cyclodextrins, calix[n]arene, cyclophane and curcubituril derivatives are also described there.

According to document [15], the dialyzable excipient is dissolved in a dialysis or substitution solution. In another embodiment, the dialyzable excipient may be present in a physical mixture with salts such as sodium chloride. To produce a ready-to-use solution, the mixture is dissolved in water for injection, possibly with the addition of additional electrolytes. Such a ready-to-use solution is also suitable as an infusion solution in accordance with WO2015091842 A2.

The teaching of document [15] also relates to a device and a method of removing protein-bound toxins by adding a dialyzable adjuvant.

The teaching of document [15] relates in particular to a device for carrying out the described method of removing protein-bound toxins, comprising an extracorporeal circuit for receiving blood to be purified and comprising a hemodialyzer and/or hemofilter, which is connected to the blood circulation, the blood circulation having upstream and optionally downstream of the hemodialyzer and/or hemofilter each at least one supply line for supplying a substitution fluid. The substitution fluid supplied upstream of the hemodialyzer and/or hemofilter via a supply line comprises the dialyzable excipient.

Today, different membranes are available for the elimination of uremic toxins by hemodialysis and hemo(dia)filtration. The membrane property plays an important role in ensuring efficient dialysis treatment, [see 1-5]. The efficiency of dialysis treatment can be assessed by determining the elimination capacity in terms of small molecules [2,4,5], usually water-soluble and not protein-bound [see 5-6]. Recent clinical publications show, however, that the biochemical changes in uremia are triggered not only by water-soluble/non-protein-bound toxins [4], but also by protein-bound substances/toxins such as p-cresol, indoxyl sulfate, hippuric acid, 3-carboxy-4-methyl-5-propyl-2-furanpropionic acid (CMPF) or phenol derivatives [2,6]. These toxins are mainly bound to albumin.

Today, p-cresol and indoxyl sulfate are the most frequently investigated protein-bound toxins with dialysis patients. Purely diffusive (HD), purely convective (HF) and diffusive/convective (HDF) dialysis cannot guarantee effective elimination. This is mainly due to the fact that—as mentioned above—the retention of essential proteins such as albumin must of course also be taken into account, and the membranes for normal use in dialysis patients do not offer this selectivity. However, since p-cresol, indoxyl sulfate and other protein-bound toxins have a high cardiovascular toxicity, this is a problem for dialysis treatment until today.

In literature, there are different papers which describe how more or less selectively uremic toxins of different molecular sizes can be adsorbed from blood, human plasma or a plasma-imitating solution.

Adsorption Based on Activated Carbon

An early example of a medically applicable activated carbon with a copolymer consisting of acrylic acid and styrene and resulting in a blood-compatible coating was patented by Sparks et al. (Sandoz AG) in 1974 [7, DD 109 363]. This polymer-enclosed activated carbon is able to adsorb uncharged low-molecular mass uremic toxins (e. g. urea or creatinine). In 2015, Tschulena et al. (Fresenius AG) patented a granule which until now is one of the most advantageous adsorber granules [8]. For this purpose, an aqueous solution of polyvinylpyrrolidone (PVP), an additional crosslinker and a radical initiator is used to "graft" an activated carbon consisting of spherical particles under heating; i.e. the polymer is firmly attached to the activated carbon and forms, together with the crosslinker, uncharged mesoporous structures through which hydrophobic and charged low-molecular weight uremic toxins can diffuse (e. g. indoxyl sulfate, p-cresol sulfate, bilirubin; Ap5A and phenylacetic acid).

In 2016, Stamatialis et al. published the development of a low-flux hollow-fiber membrane based on polyether sulfone (PES) and consisting of two combined layers—"mixed-matrix membrane" (MMM). The inner layer for blood contact consists of pure PES, whereas the outer layer is composed of a composite with activated carbon finely divided in PES. The group has shown that these membranes can be used to remove indoxyl sulfate or p-cresol sulfate (artificially added and bound to albumin) in human plasma with double the effectiveness as compared to membranes without an activated carbon layer. The effectiveness with respect to the removal of uremic toxins by adsorption on the activated carbon thus adds up to the diffusion occurring in conventional dialysis [9, 10].

Studies by Glorieux and Krieter et al. [11a and 11b] have reported that the blood plasma of a healthy person has 0.53±0.29 mg/l of indoxyl sulfate and that of a patient suffering from chronic kidney disease prior to dialysis treatment has 44.5±15.3 mg/l [11]. After dialysis treatment, this value can be reduced to ~39 mg/l according to a study by Böhringer et al [11, 12]. If the results are compared to MMM from Stamatialis et al. [9], an MMM in a dialysis treatment would be able to decrease this value to ~32 mg/l.

Adsorption Based on Porous Aryl Synthetic Resin

In 1984, Tlustakova et al. patented one of the first examples for the production of a porous adsorber based on styrene, divinylbenzene (DVB) and acrylonitrile with covalently grafted 2-hydroxyethylmethacrylate including a suitable cross-linking agent as a biocompatible layer for blood contact [13]. Filters of this type are still used today, for instance for LdL apheresis. Due to the hydrophobic character of the styrene-based resin and the substances to be removed, these adsorbers are particularly effective. More recently, the company Cytosorbents Corp. produces an adsorber for the removal of cytokines (also medium-molecular proteins with hydrophobic domains) from whole blood. The core of the particles, which is actually responsible for adsorption, is also based on a styrene DVB copolymer, and the biocompatible protective layer consists of highly porous PVP here. Thus, even cytokines with a higher molecular mass can be adsorbed (8 kDa to 100%, 18 kDa to 85% and 51 kDa to 55%) [14].

Cyclodextrin for Complex Formation (Guest Host Relationship)

In 2013, Fislage et al. (Fresenius Medical Care Deutschland GmbH) patented a completely new approach to the removal of albumin-bound toxins with a hydrophobic domain by the use of the dializable excipient cyclodextrin with a bondable cavity affine for it [15]. This invention is therefore based on a "recomplexing" in solution. 202 μmol/l of p-cresol, which is found at an increased amount in the blood of patients suffering from renal disease, were added to an artificial plasma produced from 638 μmol/l of Bovine Serum Albumin (BSA) (corresponding to 30 g/l) in buffer. This immediately forms a complex with the BSA. This solution was pumped through the lumen side of a commercially available high-flux dialyzer (type Fresenius FX60) at a flow rate of 100 ml/min. Immediately before the inlet into the dialyzer, a solution of hydroxypropyl-β-cyclodextrin (224 g/l) was continuously dosed at 10 ml/min, so that a concentration of 22.4 g/l (16 mmol/l) was achieved in the entire solution. At the outlet of the dialyzer (volume flow 110 ml/min) there was a remarkable decrease in the concentration of the p-cresol to 55% compared to the input concentration.

In 2009, Hammond et al. published the first example of an adsorber based on poly(carboxymethyl-β-cyclodextrin) [16]. This anionic polyelectrolyte was immobilized in combination with a biodegradable, cationic polyelectrolyte as an adhesion promoter on a model surface made of silicon in alternating fashion by a layer-by-layer (LbL) process. These layers were used to complex hydrophobic substances (antibiotics, Flurbiprofen and Diclofenac). The weakly negatively charged carboxyl groups on the rings of the cyclodextrin itself form the basis for the adhesion of the polymer to the substrate.

Further Methods

The binding between a protein and one of the discussed hydrophobic toxins is based on the formation of a complex which in the aqueous environment of the blood is on the side of the complex [11,12,17,18]. Indoxylsulfate, phenylacetic acid and p-cresol sulfate are present in the bound form under physiological conditions (NaCI=0.15 mol/l) with 96%, 60% and 97%, respectively. If the salt concentration is increased to the hypertonic range of, for example, 0.50 mol/l, this equilibrium is shifted to 88%, 36% and 91%, respectively. The increased salt content interferes with the interaction between toxin and protein. As a result, the low-molecular toxin can be removed through a dialysis membrane. This procedure is problematic for the patient due to physiological limitations. In the same study, Böhring et al. investigated the possibility of influencing the elimination of hydrophobic toxins with the aid of high-frequency electromagnetic fields by using the dialyzer as a dielectric between two capacitor plates or as the core of a coil in in-vitro experiments. As a result, it was found that the influence is significantly less than when using an increased salt concentration [11,12].

Disadvantages of Previous Prior Art Solutions

If activated carbon or a polymer having the tendency to hydrophobic behavior, e.g. a copolymer of styrene and divinylbenzene (Amberlite XAD-2) is used as an adsorber for removing hydrophobic, low-molecular blood toxins or cytokines, whole blood cannot be brought into direct contact with these materials. This is a big disadvantage. In order to avoid this, it can be separated with a plasma filter so that plasma isolated from solid blood components can be purified by such an adsorber and then returned. However, this method requires complex pump and hose systems [19]. Another possibility is to "mask" the base polymer with one of the above-mentioned biocompatible hydrophilic polymers to allow contact with whole blood. For such a functionalization, a chemical connection on the substrate is usually necessary by so-called "radical graft copolymerization". Realizing this is very costly. However, the protective layer represents a more or less pronounced diffusion barrier, mainly for larger molecules. The barrier is particularly pronounced in the case of the MMM proposed by Stamatialis et al. In the in-vitro experiments described, ~40 μm PES separate the proteins loaded with p-cresol on the blood side from the adsorbent layer with activated carbon on the dialysate side [9,10]. The high wall thickness of the membranes (~100 μm) also results in a thick fiber with an unfavorable ratio of the number of fibers per bundle diameter. A high material consumption for the production of the membrane is evident here and thus a higher cost factor. Conventional adsorbers with activated carbon further have the disadvantage that they are not very selective, i.e. proteins which are vital for the patients to be treated and which are present in the blood, or poorly water-soluble vitamins, are also adsorbed alongside harmful molecules. Similarly, there is no selective behavior with regard to the molecular mass of the substances to be adsorbed. In the therapy form of apheresis for the treatment of metabolic diseases of the fat balance (dyslipidemia), these effects are pushed back, because mainly the LDL etc. to be removed occupies the adsorption sites. Generally, a further disadvantage is the large blood volume of 200 to 400 ml and a high pressure loss of such an adsorber. This property leads to small possible blood flows in most products. In sum, these properties mean that the integration into an ordinary hemodialysis system is not possible.

Based on the state of the art according to WO2015091842 A2 [15], it is the task of the present invention to solve the protein-bound toxins from the albumin and then effectively remove them by dialysis without introducing additional excipients into the patient and/or the dialysis fluid, as is necessary according to the teaching of document [15].

SUMMARY OF THE INVENTION

In particular, the present invention relates to a hemocompatible adsorber for the separation of protein-bound uremic toxins contained in the blood or blood plasma of a patient and having a molecular mass of <500 g/mol regarding their carrier proteins in order to make the uremic toxins dialyzable with hemodialysis, wherein the hemocompatible material comprises a polymer based on a cyclic oligosaccharide or a derivative thereof disposed on a solid carrier component in at least one layer.

Within the scope of the present invention, the uremic toxins are selected from the group consisting of p-cresol, indoxyl sulfate, phenol, phenol derivatives, homocysteine, urofuranic acids, in particular 3-carboxy-4-methyl-5-propyl-2-furanopropionic acid, hippuric acid and p-hydroxyhippuric acid.

In a preferred embodiment, the adsorber according to aspects of the invention is particularly effective when the uremic toxins to be removed are bound to human albumin as carrier protein.

In the context of present invention, it is preferred to use a hemocompatible adsorber in which the cyclic oligosaccharide-based polymer is selected from the group consisting of: polycyclodextrins, poly-β-cyclodextrins, poly(carboxymethyl-β-cyclodextrin and poly(trimethylammonium-β-cyclodextrin and cyclodextrins condensed with epichlorohydrin.

Within the context of the present invention, the solid carrier component is preferably selected from the group consisting of: a preferably non-woven fabric material, a hollow fiber or flat membrane or other porous materials based on polyether sulfone [PES], polysulfone [PSU], polyether ether ketones [PEEK], polyphenylsulfone [PPSU], Polyoxymethylene [POM], polyphenol, polyamides, in particular nylon, polystyrene, polyacrylate, polycarbonate or polymers containing acrylonitrile or a methylallylsulfonate salt or copolymers thereof.

The polymer on the basis of a cyclic oligosaccharide or a derivative thereof is typically applied within the scope of the present invention to the solid carrier component in a number of layers using a layer-by-layer technique [LbL technique]. The LbL technique is well known to the expert, for example from [16].

A particular advantage of the hemocompatible adsorber according to aspects of the invention is produced if it is designed as a separate cartridge arranged upstream of a dialyzer of a hemodialysis system, in which a fabric, particularly a non-woven fabric disposed therein is coated with the polymer.

A further special advantage of the hemocompatible adsorber according to aspects of the invention is produced if it is integrated as a non-woven fabric coated with the polymer in a blood cap of a dialyzer of a hemodialysis system.

A hemocompatible adsorber described in the context of present invention is one that is integrated into the pore system of the hollow fiber membranes of a dialyzer of a hemodialysis system.

The present invention also relates to a hemodiafiltration apparatus comprising an extracorporeal circuit for receiving blood to be purified and a hemodialyzer and/or hemofilter connected to the blood circulation of a patient;

wherein a hemocompatible adsorber is provided for the separation of protein-bound uremic toxins contained in the blood or blood plasma of a patient and having a molecular mass of <500 g/mol regarding their carrier proteins; and wherein the hemocompatible adsorber, which is disposed on a solid carrier component in at least one layer on the blood side within the hemodialyzer, comprises a polymer based on a cyclic oligosaccharide or a derivative thereof.

The present invention thus describes an adsorber for the selective and effective removal of albumin-bound toxins with hydrophobic and/or charged domains up to a molecular mass of ~500 Da (e.g. indoxyl sulfate, p-cresol, hippuric acid, p-hydroxyhippuric acid or phenylacetic acid) to support ordinary extracorporeal blood treatment (e. g. hemodialysis or liver dialysis).

The adsorber consists of a hemocompatible polymer based on cyclodextrin, which is applied to a porous material with a large surface area using LbL technology. The ideal carrier is a non-woven fabric with a suitable mesh size. This coated fabric can be connected in series in a small cartridge upstream of the dialyzer or integrated into the blood caps of the dialyzer. Another useful option is to coat the entire accessible surface area of a high-flux hollow-fiber membrane for hemodialysis with the hemocompatible polymer. The polymer should preferably consist, on the one hand, of the above-mentioned poly(carboxymethyl-β-cyclodextrin) first introduced by Hammond et al [16] as an anionic polyelectrolyte. On the other hand, it should consist of the cationic adhesion promoter polyethylene imine (PEI) or ideally a cationic cyclodextrin counterpart, such as the poly(trimethylammonium-62-cyclodextrin) proposed recently by Morin et al [20]. A clear advantage of the latter polyelectrolyte is that it not only acts as a bonding agent for the LbL process like PEI, but also contains cyclodextrin by itself. Thus, the capacity of the adsorber increases with each applied layer up to the desired point. In principle, these two polyelectrolytes can be produced simply by condensing correspondingly modified cyclodextrin with epichlorohydrin. These syntheses can be carried out in aqueous solutions or also in organic solvents under simple reaction conditions [21,22,23]. Cravotto et al. and Hapiot et al. further disclose a new possibility for the modification of cyclodextrins as a solid-phase reaction without water with the aid of a ball mill [24,25].

In order to achieve the best possible transition of the blood toxin from albumin to the adsorber, the binding constant of the adsorber to the corresponding toxin must be large enough. Under physiological conditions (0.15 mol/l NaCl), this value is between albumin and indoxyl sulfate Ks=48,000 L/mol [12]. In comparison, (native) cyclodextrin in solution has only a binding constant of Ks=12,000 L/mol. However, according to the patent of Fislage et al. it could be shown that under the experimental conditions a major part of 55% of a toxin (p-cresol) can still be removed [15]. With an approximate filling volume of 100 mL of all the lumens of a dialyzer with an effective membrane area of 1.6 m$^2$, the dwell time of the model plasma is ~55 s at 110 ml/min. This time is apparently sufficient to allow the new equilibrium adjustment to take place after diffusive removal of the first "recomplexed" toxins and thus achieve an effective removal. The complex of p-cresol and hydroxypropyl β-cyclodextrin has a molecular mass of ~1,500 g/mol and is therefore easily dialyzable in contrast to the albumin complex (approx. 65,200 g/mol). Due to this fact, two further aspects make the adsorber proposed in the context of present invention far more effective: 1) The cationic poly(trimethylammonium-β-cyclodextrin) or a multi-substituted derivative thereof contains a ligand which increases the binding constant of the adsorber in comparison to native cyclodextrin by the factor of up to 3,000 (Ks=12,000 L/mol vs. 3,410,000 L/mol; both in solution)—due to the quaternary ammonium residue [18]; 2) The binding constant of an adsorber generally increases by the factor of 10 to 15 when it is present as a solid state or swellable film, compared to a guest-host complex in solution [26]. The reason for this is the additional, physically caused adsorption enthalpy on the solid state. In the blood of people with chronic kidney disease, among other substances, the following albuminous toxins are mainly found in the blood: p-cresol with 41.0±13.3 mg/l blood, indoxyl sulfate with 44.5±15.3 mg/l blood, hippuric acid with 87.2±61.7 mg/l blood and p-hydroxyhippuric acid with 18.3±6.6 mg/l blood [11].

Assuming that the blood of a healthy person contains by contrast only 1 to 5% of the concentrations of the substances mentioned [11], only an amount of ~1.4 g of the described carrier-bound polymer with adsorbing effect, related to "native" β-cyclodextrin cross-linked with epichlorohydrin, is required per liter of blood to be purified.

There is currently no selective adsorber for protein-bound blood toxins up to ~500 g/mol. The adsorber according to aspects of the invention can be immobilized on any substrate with variable capacity and affinity. It is distinguished by the fact that compared to other adsorbers, only a small amount of functional polymer is required.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
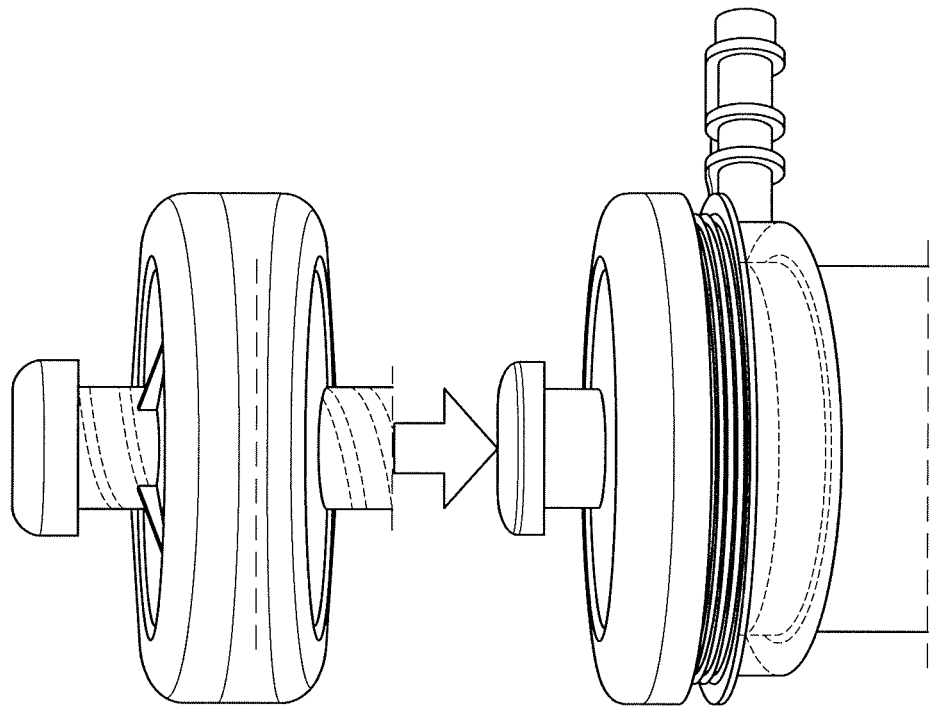
FIG. 1 illustrates a small additional blood volume for series connection of a separate cartridge to a dialyzer.
Figure 2:
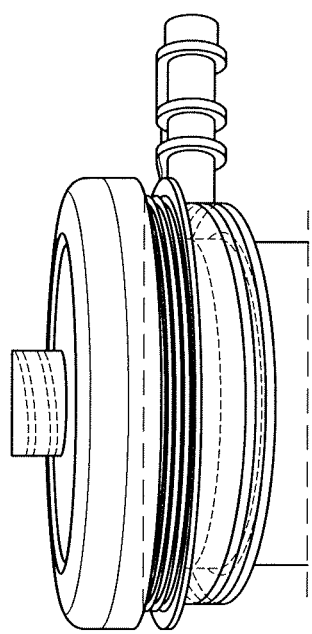
FIG. 2 illustrates that no additional blood volume for series connection of a separate cartridge to a dialyze is required if it is used in the blood caps of the dialyzer.
Figure 3:
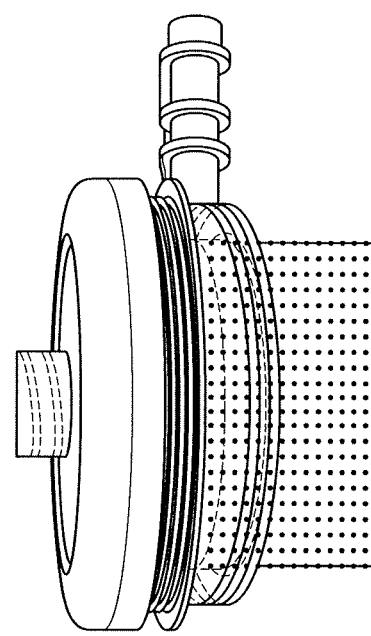
FIG. 3 illustrates no additional blood volume for series connection of a separate cartridge to a dialyze is required if it is used on the entire surface of the hollow fiber membrane.

Either a small additional blood volume is required for series connection of a separate cartridge to a dialyzer (FIG. 1) or no additional blood volume is required if it is used in the blood caps of the dialyzer (FIG. 2) or on the entire surface of the hollow fiber membrane (FIG. 3). Furthermore, the adsorber does without a diffusion-inhibiting protective layer, as the material itself is suitable for direct blood contact.

In principle, the innovative adsorber can be used for any dialysis treatment, since toxins <500 g/mol that are difficult to dialyze and place a heavy burden on every patient can be effectively removed. It can be integrated in the desired quantity into a hemodialysis system without affecting the function, i.e. ideally on a non-woven fabric in the blood caps (FIG. 2) without high pressure loss.

Cyclodextrins are known and accepted in the pharmaceutical industry and are used as "excipients" in the manufacture of drugs (injections, tablets and ointments) to dissolve water-insoluble drugs and thus make them biologically available.

Due to the chemical properties of modified poly-(cyclodextrin), a 15 to 200-fold increase in the adsorption rate of hydrophobic toxins in aqueous systems can be achieved with suitable preparation as compared to activated carbon [23, 27].

Furthermore, no vital minerals, amino acids or vitamins are removed from the blood.

This invention therefore describes a new adsorber for the effective removal of protein-bound blood toxins up to 500 g/mol as a support for conventional hemodialysis. It is based on modified cyclodextrin and can be integrated into any part of a hemodialysis system using LbL technology.

The invention claimed is:

1. A hemodiafiltration apparatus comprising:
    an extracorporeal circuit for receiving blood to be purified;
    at least one of a hemodialyzer or hemofilter connected to the blood circulation of a patient; and
    a hemocompatible adsorber for separating protein-bound uremic toxins contained in the blood or blood plasma of the patient and having a molecular mass of <500 g/mol regarding their carrier proteins;
    wherein the hemocompatible adsorber, which is disposed on a solid carrier component in at least one layer on a blood side within the hemodialyzer or hemofilter, comprises a polymer based on a cyclic oligosaccharide or a derivative thereof,
    wherein the polymer is disposed on the solid carrier component using a layer by layer (LBL) technology,
    wherein the polymer for a first layer of the LBL technology is an anionic polyelectrolyte,
    wherein the polymer for a second layer disposed on the first layer is a cationic counterpart, and
    wherein the hemocompatible adsorber is integrated as the solid carrier component coated with the polymer in a blood cap of the hemodialyzer.

2. The hemodiafiltration apparatus according to claim 1, wherein the uremic toxins are selected from the group consisting of: p-cresol, indoxyl sulfate, phenol, phenol derivatives, homocysteine, urofuranic acids, in particular 3-carboxy-4-methyl-5-propyl-2-furanopropionic acid, hippuric acid and p-hydroxyhippuric acid.

3. The hemodiafiltration apparatus according to claim 1, wherein the carrier protein is human albumin.

4. The hemodiafiltration apparatus according to claim 1, wherein the polymer based on cyclic oligosaccharides is selected from the group consisting of: polycyclodextrins, poly-β-cyclodextrins, poly(carboxymethyl-β-cyclodextrin) and poly(trimethylammonium-β-cyclodextrin) or their derivatives and cyclodextrins fused with epichlorohydrin.

5. The hemodiafiltration apparatus according to claim 1, wherein the solid carrier component is selected from the group consisting of: a preferably non-woven fabric material, a hollow fiber or flat membrane or other porous materials based on polyether sulfone [PES], polysulfone [PSU], polyether ether ketones [PEEK], polyphenylsulfone [PPSU], polyoxymethylene [POM], polyphenol, polyamides, in particular nylon, polystyrene, polyacrylate, polycarbonate or polymers containing acrylonitrile or a methylallylsulfonate salt or copolymers thereof.

6. The hemodiafiltration apparatus according to claim 1, wherein the solid carrier component is a porous material based on polyethersulfone [PES], polysulfone [PSU], polyether ether ketones [PEEK], polyphenylsulfone [PPSU], polyoxymethylene [POM], polyphenol, polyamides, in particular nylon, polystyrene, polyacrylate, polycarbonate or polymers containing acrylonitrile or a methylallylsulfonate salt or copolymers thereof.

7. The hemodiafiltration apparatus according to claim 1, wherein the anionic polyelectrolyte is poly(carboxymethyl-β-cyclodextrin).

8. The hemodiafiltration apparatus according to claim 1, wherein the cationic counterpart is polyethylene imine or poly(trimethylammonium-6-cyclodextrin).

9. A hemodiafiltration apparatus comprising:
    an extracorporeal circuit for receiving blood to be purified;
    at least one of a hemodialyzer or hemofilter connected to the blood circulation of a patient; and
    a hemocompatible adsorber for separating protein-bound uremic toxins contained in the blood or blood plasma of the patient and having a molecular mass of <500 g/mol regarding their carrier proteins;
    wherein the hemocompatible adsorber, which is disposed on a solid carrier component in at least one layer on a blood side within the hemodialyzer or hemofilter, comprises a polymer based on a cyclic oligosaccharide or a derivative thereof,
    wherein the polymer is disposed on the solid carrier component using a layer by layer (LBL) technology,
    wherein the polymer for a first layer of the LBL technology is an anionic polyelectrolyte,
    wherein the polymer for a second layer disposed on the first layer is a cationic counterpart, and
    wherein the hemocompatible adsorber is integrated into a pore system of hollow fiber membranes of the hemodialyzer.

10. The hemodiafiltration apparatus according to claim 9, wherein the anionic polyelectrolyte is poly(carboxymethyl-β-cyclodextrin).

11. The hemodiafiltration apparatus according to claim 9, wherein the cationic counterpart is polyethylene imine or poly(trimethylammonium-6-cyclodextrin).

12. The hemodiafiltration apparatus according to claim 9, wherein the uremic toxins are selected from the group consisting of: p-cresol, indoxyl sulfate, phenol, phenol derivatives, homocysteine, urofuranic acids, in particular 3-carboxy-4-methyl-5-propyl-2-furanopropionic acid, hippuric acid and p-hydroxyhippuric acid.

13. The hemodiafiltration apparatus according to claim 9, wherein the carrier protein is human albumin.

14. The hemodiafiltration apparatus according to claim 9, wherein the polymer based on cyclic oligosaccharides is selected from the group consisting of: polycyclodextrins, poly-β-cyclodextrins, poly(carboxymethyl-β-cyclodextrin) and poly(trimethylammonium-β-cyclodextrin) or their derivatives and cyclodextrins fused with epichlorohydrin.

15. The hemodiafiltration apparatus according to claim 9, wherein the solid carrier component is selected from the group consisting of: a preferably non-woven fabric material, a hollow fiber or flat membrane or other porous materials based on polyether sulfone [PES], polysulfone [PSU], polyether ether ketones [PEEK], polyphenylsulfone [PPSU], polyoxymethylene [POM], polyphenol, polyamides, in particular nylon, polystyrene, polyacrylate, polycarbonate or polymers containing acrylonitrile or a methylallylsulfonate salt or copolymers thereof.

16. The hemodiafiltration apparatus according to claim 9, wherein the solid carrier component is a porous material based on polyethersulfone [PES], polysulfone [PSU], polyether ether ketones [PEEK], polyphenylsulfone [PPSU], polyoxymethylene [POM], polyphenol, polyamides, in particular nylon, polystyrene, polyacrylate, polycarbonate or polymers containing acrylonitrile or a methylallylsulfonate salt or copolymers thereof.

* * * * *